United States Patent [19]
Rokugawa

[11] Patent Number: 4,623,618
[45] Date of Patent: Nov. 18, 1986

[54] SIMULTANEOUS QUANTITATIVE IMMUNOASSAY FOR DIFFERENT ANTIGENS OR ANTIBODIES

[75] Inventor: Kyuji Rokugawa, Ootawara, Japan

[73] Assignee: Tokyo Shibaura Denki Kabushiki Kaisha, Kawasaki, Japan

[21] Appl. No.: 547,353

[22] Filed: Oct. 31, 1983

[30] Foreign Application Priority Data

Nov. 5, 1982 [JP] Japan .................. 57-195115

[51] Int. Cl.⁴ .................. C12Q 1/68; G01N 33/54
[52] U.S. Cl. .................. 435/6; 435/7; 436/513; 436/519; 436/520; 436/522; 436/543; 436/547; 436/523; 436/819; 436/829
[58] Field of Search .................. 435/7, 6; 436/522, 519, 436/523, 819, 829

[56] References Cited

U.S. PATENT DOCUMENTS

| | | | |
|---|---|---|---|
| 3,850,578 | 11/1974 | McConnell . | |
| 4,235,792 | 11/1980 | Hsia et al. | 260/403 |
| 4,292,403 | 9/1981 | Duermeyer | 435/7 |
| 4,338,094 | 7/1982 | Elahi . | |
| 4,342,826 | 8/1982 | Cole | 435/7 |

FOREIGN PATENT DOCUMENTS

| | | |
|---|---|---|
| 0014530 | 8/1980 | European Pat. Off. . |
| 2051357 | 1/1981 | United Kingdom . |

OTHER PUBLICATIONS

Haxby-Proc. N.A.S., vol. 61 (1968), pp. 300–307.
D'Orazlo et al.-Anal. Chem., vol. 49, No. 13 (Nov. 1977), pp. 2083–2086.
Cole-International Patent Document-WO81/02344, (Aug. 20, 1981), pp. 1–43.

Primary Examiner—Sam Rosen
Attorney, Agent, or Firm—Cushman, Darby & Cushman

[57] ABSTRACT

An immunoassay by which a plurality of kinds of antigens or antibodies in one test sample may be simultaneously quantified. Each of a plurality of kinds of microcapsules is first provided for each kind of a plurality of antigens or antibodies to be quantified such that the microcapsules bind an antibody or antigen specific to one kind of the plurality of antigens or antibodies to be quantified. The microcapsules are formed of a membrane capable of being lysed by the complement activity, and each kind of microcapsules contains therein a substance that is quantifiable and does not interact with another quantifiable substance contained in other kinds of microcapsules. The plurality of kinds of microcapsules are mixed with a test sample and complement, and the quantifiable substances are released from the microcapsules upon lysis of the microcapsules by the complement activity. The quantifiable substances are then quantified.

8 Claims, 2 Drawing Figures

I OBALBUMIN
II CHYMOTRYPSINOGEN
III CHTOCHROME C.

SIMULTANEOUS QUANTITATIVE IMMUNOASSAY FOR DIFFERENT ANTIGENS OR ANTIBODIES

BACKGROUND OF THE INVENTION

I. Field of the Invention

The present invention relates to an immunoassay.

II. Description of the Prior Art

Radioimmunoassay (RIA) for quantifying a specific antigen or antibody in a test sample is known as a conventional immunoassay. The RIA utilizes the antigen-antibody reaction of the antigen (or antibody) in the test sample collected from a patient with a corresponding antibody (or antigen) labeled with a radioisotope. An enzyme immunoassay for quantifying a specific antigen (or antibody) in a test sample is also well known. An antigen-antibody complex is produced by the antigen-antibody reaction between an antibody (or antigen) labeled with an enzyme and the corresponding antigen (or antibody) in the test sample collected from a patient. The antigen-antibody complex is quantified using the enzyme reaction of the marker enzyme.

These methods, however, can quantify only one kind of antigen (or antibody) at a time, and cannot quantify a plurality of kinds of antigens (or antibodies) simultaneously. Accordingly, for example, immunoassay procedures must be repeated three times where three different kinds of antigens (or antibodies) are to be quantified.

In order to diagnose infections diseases, chronic hepatic disorder, immune diseases or malignant tumors, each of the human immunoglobulins in blood, namely, IgG, IgA and IgM, are quantified. Similarly, the diagnosis of various cancers is made by quantifying various cancer markers in a test sample, such as α-fetoprotein, carcino embryonic antigen (CEA), C-reactive protein and ferrittin. Further, in order to diagnose cancers or various organic disorder, isozymes such as amylase and creatine kinase are seperately quantified recently. A strong demand accordingly exists for the provision of an immunoassay method capable of simultaneously quantifying more than one kind of antigen (or antibody).

SUMMARY OF THE INVENTION

It is, therefore, an object of the present invention to provide an immunoassay capable of simultaneously quantifying a plurality of kinds of antigens or antibodies contained in a test sample.

In the immunoassay according to the present invention, a plurality of microcapsules having on their outer surfaces one kind of antibody (or antigen) specific to one kind of antigen (or antibody) of the different kinds of antigens (or antibodies) to be quantified, are provided for each of the different kinds of antigens (or antibodies) to be quantified. Thus, a plurality of kinds of microcapsules are provided, each kind of microcapsule having one kind of antibody (or antigen) on its outer surface, and each kind of microcapsule comprising a plurality of microcapsules. Each microcapsule is formed of a membrane which can be lysed by complement activity, and each kind of microcapsule contains therein a quantifiable substance which is different from a quantifiable substance contained in a different kind of microcapsule. These substances do not interact with each other.

A test sample which may contain a plurality of kinds of antigens (or antibodies) to be quantified is mixed with above-mentioned a plurality of kinds of microcapsules and complement. This mixture allows an antigen-antibody complex to be formed between the antigen (or antibody) in the test sample and the corresponding antibody (or antigen) bound on the outer surface of each microcapsule. Such an antigen-antibody complex causes activation of the complement so that the membranes of the microcapsules having such an antigen-antibody complex on their outer surfaces are lysed, whereby the respective quantifiable substances contained therein are released therefrom.

The quantifiable substances released from the microcapsules are then quantified. The amount of each kind of antigen (or antibody) in the test sample is proportional to the amount of the corresponding antigen-antibody complex formed between the antigen (or antibody) and the corresponding antibody (or antigen). The microcapsules having the antigen-antibody complex bound on their outer surfaces are lysed by the complement activity, releasing the quantifiable substances contained therein. As a result, the amount of each kind of antigen (or antibody) present in the test sample is in proportion to the amount of the corresponding quantifiable substance released from the corresponding microcapsules. Therefore, the amount of antigen (or antibody) present in the test sample can be determined by quantifying the amount of the substances released from the microcapsules. Since a plurality of kinds of microcapsules respectively corresponding to the plurality of kinds of antigens or antibodies to be quantified are mixed with a test sample, a plurality of kinds of quantifiable substances respectively corresponding to the different kinds of antigens (or antibodies) are released. Accordingly, the quantitative analysis of each kind of the plurality of kinds of quantifiable substances allows the amount of each of the plurality of kinds of antigens (or antibodies) in the test sample to be quantified. The quantitative analysis of the plurality of kinds of quantifiable substances may be carried out simultaneously by means of chromatographic techniques.

The present invention thus provides simultaneous quantitative analysis of a plurality of kinds of antigens (or antibodies) contained in a test sample.

DETAILED DESCRIPTION OF THE PREFERRED EMBODIMENTS

Figure 1:
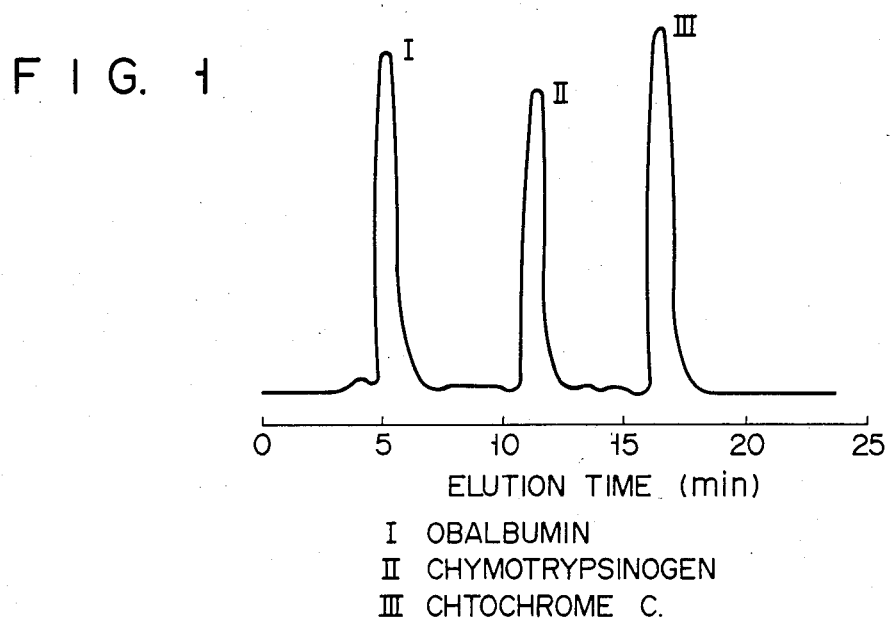
FIG. 1 shows a typical elution pattern of the markers used in the immunoassay of the present invention.

The reagent to be used in the immunoassay according to the present invention comprises microcapsules formed of a membrane that can be lysed by complement activity. In the method according to the present invention, any microcapsule may be employed that can be lysed by the complement activity, that allows an antibody (or antigen) to be bound on the outer surface thereof, and allows a quantifiable substance to be encapsulated therein. A preferred example of such a microcapsule is a sheep red blood cell ghost. An artificial membrane such as liposome may also be employed.

An antibody (or antigen) that specifically combines with one kind of antigen (or antibody) of a plurality of kinds of antigens (or antibodies) to be quantified is bound to the outer surface of each microcapsule. Such microcapsules are provided for each kind of antigens (or antibodies) to be quantified. For example, where human immunoglobulins, i.e., IgG, IgA and IgM, are to be quantified, three different kinds of microcapsules are prepared which respectively have an anti-IgG antibody, an anti-IgA antibody and an anti-IgD antibody bound on to the outer surfaces.

Each kind of the microcapsules contains different kind of quantifiable substance therein that causes no interaction with the any of other quantifiable substances. The substance may be selected from an amino acid, a sugar, a carboxylic acid, a peptide, a polysaccharide, an enzyme, a protein, and a nucleic acid. The substance should be selected from those which will not leak from the microcapsule. One of the water-soluble proteins, enzymes, polysaccharides, nucleic acids and other macromolecules each having a different molecular weight may preferably be contained in each kind of microcapsules. One example of such combination of water-soluble macromolecules may be cytochrome c (molecular weight: 12,400), ovalbumin (molecular weight: 45,000), chymotrypsinogen (molecular weight: 25,000), bovine serum albumin (molecular weight: 67,500) and carboxymethyl cellulose (molecular weight: 75,000).

A diffcrent kind of substance is encapsulated in each kind of microcapsule. That is to say, where a human immunoglobulin is to be quantified, for example, ovalbumin may be encapsulated in microcapsules having an anti-IgG antibody bound thereto, chymotrypsinogen in microcapsules having an anti-IgA antibody bound thereto, cytochrome c in microcapsules having an anti-IgM antibody bound thereto.

Since these quantifiable substances are to be simultaneously quantitatively analyzed, they must not interact with each other.

The concentration of the quantifiable substances encapsulated in the microcapsules may be controlled, and conveniently selected according to the immunoassay involved. In order to improve the sensitivity of the quantitative analysis, higher concentrations are preferred. In general, the concentration is preferably $10^{-5}$ M or more. However, as immunoglobulins in blood, where it is expected that concentrations of the different immunoglobulins in the test sample will differ to a large extent, it is preferred that the concentrations of the quantifiable substances in the microcapsules corresponding to each of the immunoglobulins be substantially proportional to the concentrations of the respective immunoglobulins in the test sample. Then, the amount of each substance to be analyzed will be substantially the same, so that when these substances are simultaneously quantified by means of chromatography or the like, the sensitivity of the analysis can be improved. For example, in the case where ovalbumin is encapsulated in microcapsules having an anti-IgG antibody bound thereto, chymotrypsinogen in microcapsules having an anti-IgA antibody bound thereto, cytochrome c in microcapsules having an anti-IgM antibody bound thereto, the concentrations of chymotrypsinogen and cytochrome c are preferably from 2 to 10 times the concentration of ovalbumine. The reason is that the concentrations of IgG, IgA and IgM in the blood are 10–17, 0.9–3.3 and 0.5–3.0 mg/ml, respectively, so that the amount of each substance to be analyzed becomes almost equal by varying the concentrations as set forth hereinabove.

The microcapsules having an antibody (or antigen) specific to one of the plurality of kinds of antigens (or antibodies) to be quantified bound to their outer surfaces and containing a quantifiable substance such as a protein therein may be prepared according to the following procedures. As an example, a description is made of the case where sheep red blood cell ghosts are employed as microcapsules, an anti-IgG antibody is used as an antibody to be bound to the microcapsules, and ovalbumin is used as a quantifiable substance.

IgG is administered to an animal such as a rabbit, goat, mouse or rat through, for example, subcutaneous routes, whereby an anti-IgG antibody is produced in the animal's body. Blood is collected from the animal about one week after the administration, and a serum is obtained which is anti-serum containing the anti-IgG antibody. In order to improve a specificity of the antigen-antibody reaction, the anti-serum may be further purified according to a conventional technique.

On the other hand, blood is collected from a sheep and then red blood cells are obtained. The collected red blood cells are then suspended in an isotonic solution such as a buffer solution containing 0.15 M sodium chloride (pH 7).

The anti-serum containing the anti-IgG antibody is then mixed with the suspension of sheep red blood cells in the presence of chromium chloride. This allows the anti-IgG antibody to be adsorbed on the cell membranes of the sheep red blood cells, thereby producing an isotonic solution containing sheep red blood cells having the anti-IgG antibody bound on the outer surfaces of the cell membranes. A di-valent reagent such as glutaraldehyde or succinic anhydride or a peptide reagent such as Woodward's Reagent can also be used instead of chromium chloride to cause the antibody (or antigen) to be readily bound on the membrane surfaces.

Ovalbumin is added to an isotonic PBS solution to a concentration of about 200 $\mu$M. This solution and the red blood cell suspension are mixed and the mixture is then placed in a semipermeable membrane tube with one end closed. It is then subjected to dialysis against a hypotonic solution, whereby hemoglobin and mitochondria in the red blood cells are transferred to the outside of the red blood cells through pores of the cell membranes which are formed due to the difference of osmosis, and ovalbumin is introduced into the red blood cells in their place. The cell membranes are reformed by a subsequent dialysis against an isotonic solution.

According to the method of the present invention, a plurality of kinds of microcapsules mentioned above are mixed with a test sample that may contain a plurality of kinds of antigens (or antibodies) to be quantified, together with complement. Then, antigen-antibody complexes are formed between each kind of antigen (or antibody) in the test sample and the antibody (or antigen) on the microcapsules specific thereto. Each such antigen-antibody complex activates the complement, which in turn lyses the microcapsules having the antigen-antibody complex on their surface. As a consequence, the quantifiable substances contained within the microcapsules are released therefrom. As complement, there may be used one contained in blood of an animal. For example, guinea pig serum may be used as it stands as a complement-containing solution.

The plurality of kinds of quantifiable substances released are then quantitatively analyzed. The quantitative analysis may be appropriately carried out, depending on the kinds of substances used, by means of chromatography such as gas chromatography or liquid chromatography, an electrochemical technique such as a procedure using an ion-selective electrode, an optical procedure such as spectroscopic analysis, or any other means. Where water-soluble high molecular weight substances are to be quantified, each of the substances may be individually quantified by a molecular sieve. In this case, a plurality of kinds of macromolecules can be simultaneously quantified in a short time by using a high performance liquid chromatography.

It is noted that the amount of an antigen (or antibody) present in a test sample is proportional to the amount of the antigen-antibody complex formed between the antigen (or antibody) and the corresponding antibody (or antigen). The microcapsules having antigen-antibody complexes on the outer surfaces are lysed by the complement activity and the quantifiable substances contained in the microcapsules are released. Therefore, if the amount of an antigen (or antibody) in a test sample is large, the number of corresponding micromolecules to be lysed is correspondingly large. As a result, the amount of each kind of substance released from the microcapsules increases with the amount of the corresponding antigen (or antibody) in the test sample. Thus, the amount of the antigen (or antibody) present in the test sample is proportional to the amount of the quantifiable substance released from the microcapsules. Accordingly, the amount of each of the plurality of kinds of antigens or antibodies to be quantified may be determined by quantifying each of the plurality of kinds of substances released. The determination of an unknown amount of an antigen (or antibody) present in the test sample from the amount of a corresponding substance released from the microcapsules may be conducted on the basis of a calibration curve. The calibration curve may be prepared according to a well-known method. That is to say, a known amount of a sample containing a known concentration of an antigen (or antibody is) mixed with a predetermined amount of microcapsules having the corresponding antibody (or antigen), and the amount of the quantifiable substance released from the microcapsules is determined. This procedure is repeated by varying the concentrations of the antigen (or antibody) in the test sample. The calibration curve may be formed by plotting the concentrations of the antigen (or antibody) present in the test sample along the axis of abscissa and the amounts of the substance released from the microcapsules along the axis of ordinate. An unknown concentration of the antigen (or antibody) in a test sample can then be determined from the calibration curve by plotting an amount of the substance released from microcapsules.

EXAMPLE 1

A commercially available sheep red blood cell suspension was washed two times by a PBS (137 mM NaCl, 2.7 mM KCl, 8.1 mM Na$_2$HPO$_4$, 1.5 mM KH$_2$PO$_4$, 4 mM MgCl$_2$, pH 7.2) through centrifugation (3,000 rpm, 10 min.) at room temperature, and the red blood cells were resuspended in the same PBS to attain a cell concentration of 20% (about $6 \times 10^9$ cells/ml).

Ovalbumin (M.W. 45,000), Cytochrome c (M.W. 12,400) and Chymotrypsinogen (M.W. 25,000) which were to be used as markers were dissolved in the PBS separately to obtain three marker solutions having concentrations of 0.2 mM, 1 mM and 1 mM respectively.

One milliliter of the washed 20% sheep blood cell suspension was added to each of the three marker solutions of 10 ml. These three mixtures were separately transferred to dialysis tubes. After the end portions of the tubes were tied, the tubes were put in a 1 l of 6 times-diluted rPBS (2.7 mM NaCl, 137 mM KCl, 8.1 mM Na$_2$HPO$_4$, 1.5 mM KH$_2$PO$_4$, 4 mM MgCl$_2$, pH 7.2) and the mixtures were dialyzed against the rPBS until hemolysis was completed. After the hemolysis was completed, the tubes were put in the rPBS (isotonic) and the cell suspensions were further dialysed for 15 to 20 minutes. Then each red blood cell suspension was transferred to a centrifugation tube and was washed 5 times with a physiological saline through centrifugation to remove the excess marker. The precipitations of the red blood cells were separately resuspended in the PBS to attain a cell concentration of 2%. The sheep red blood cells containing respective markers thus obtained were stored at 5° C. until the time of use.

Meanwhile, a portion of each of the marker-containing red blood cell suspensions was taken out and the cells were destroyed to release the marker by freeze lysis using dry ice-acetone. Each marker released from the cells was quantified by a High Performance Liquid Chromatography (HPLC) hereinafter described. The concentrations of ovalbumin, cytochrome c and chymotrypsinogen in the red blood cells were 85 $\mu$M, 923 $\mu$M and 874 $\mu$M respectively.

EXAMPLE 2

The sheep red blood cells each containing ovalbumin, cytochrome c, or chymotrypsinogen as a marker prepared in Example 1 were collected by centrifugation (3,000 rpm, 10 min. at room temperature) and supernatant in the centrifugation tubes were removed. To each packed microcapsules thus obtained, an antibody solution (100 $\mu$g/ml in saline) hereinafter described of 5 times volume and chromium chloride solution (0.5 mM in saline) of 6 times volume were added and was allowed to react for 1 hour at 30° C. with stirring. Specifically, anti-human IgG antibody solution was added to the packed microcapsules containing ovalbumin, anti-human IgM antibody solution was added to the packed microcapsules containing cytochrome c, and anti-human IgA antibody solution was added to the packed microcapsules containing chymotrypsinogen. Every antibody was obtained from rabbits. After completion of the reaction, each mixture was centrifuged and the supernatant was removed. Each precipitation of microcapsules was further washed 5 times with a physiological saline. The antibody-coated microcapsules thus obtained were resuspended in a physiological saline at a concentration of 2%. These suspensions were stored at 5° C. until the time of use.

EXAMPLE 3

Equal volume of the three kinds of microcapsules obtained in Example 2 were mixed together. Human IgG, IgM and IgA were dissolved in a physiological saline at a concentration of 2,000 ng/ml, 500 ng/ml and 500 ng/ml respectively. Thus, a standard antigen solution containing three kinds of antigens was prepared. This standard antigen solution was serially diluted with a physiological saline to provide 10 serial dilutions of the standard antigen solution.

One hundred microliters of the suspension of the mixed microcapsules was taken in a test tube, and 100 $\mu$l of the standard antigen solution and 2,000 $\mu$l of a gelatin-Veronal buffer (pH 7.4) were added thereto. With mild stirring, the mixture was allowed to react at 37° C.

After 10 minutes, 1,000 μl of a 50 times diluted-guinea pig serum (complement) was added to the reaction mixture and the reaction mixture was allowed to further react for 30 minutes at 37° C. After the completion of reaction, the reaction mixture was immediately centrifuged (3,000 rpm, 10 min. 0° C.) and the supernatant was transferred to another test tube. Three hundred microliters of the supernatant was taken by a microsyringe and was applied to a HPLC. The same procedure was repeated for every 10 dilutions of the standard antigen solution.

The HPLC was manufactured by Toyo Soda Co., Ltd. and sold under the trade name of HLC803. The column used was for gel filtration, which is sold under the trade name of G2000SW. A 0.06 M phosphate buffer containing 0.1 M KCl (pH 7.0) was used as a eluting solution. The pressure and the flow rate employed were 110 kg/cm$^2$ and 1.0 ml/min. respectively. The markers were quantified by measuring the absorbance at 280 nm.

Figure 2:
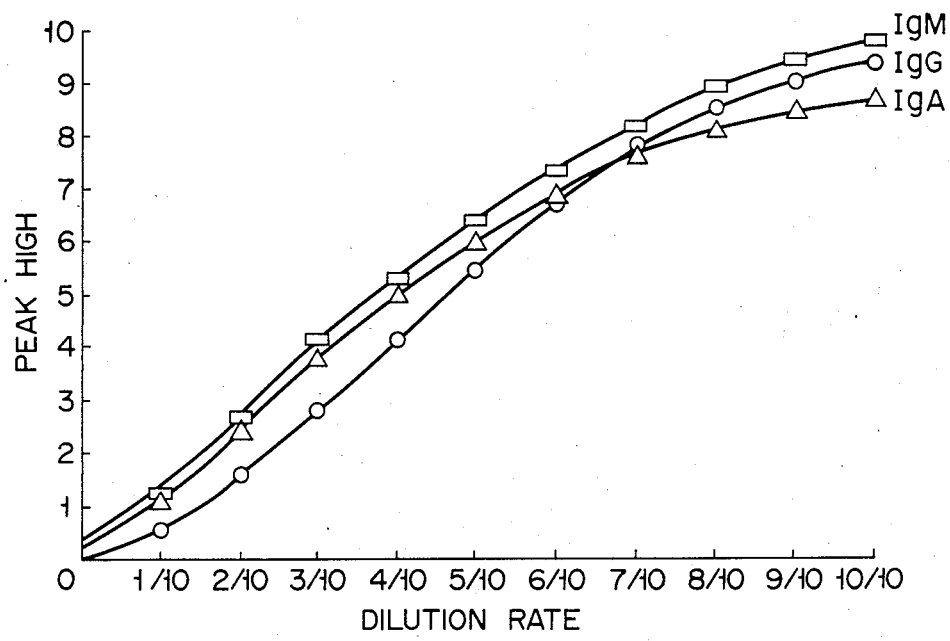
FIG. 2 shows calibration curves for three different antigens, obtained in an embodiment of the present invention.

The typical elution pattern in this experiment is shown in FIG. 1. Such an elution pattern was obtained for every 10 serial dilutions of the standard antigen solution. By plotting the peak of these elution curves, calibration curves shown in FIG. 2 were obtained. It was confirmed in advance that the anti-IgG antibody, anti-IgM antibody and anti-IgA antibody used have substantially no cross reactivity against other antigens.

EXAMPLE 4

Normal human serum was diluted in 20,000 times with a physiological saline and IgG, IgM and IgA were simultaneously quantified by the same procedure as in Example 3. The concentration of each immunoglobulin was determined using the calibration curve shown in FIG. 2. To determine the reproducibility of the immunoassay of the present invention, the same procedure was repeated 10 times. The obtained mean value ($\bar{X}$), standard deviation (S.D.) and coefficient of variation (C.V.) are shown in the following table.

| The Reproducibility of the Simultaneous Quantification of IgG, IgM and IgA in Human Serum | | | | |
|---|---|---|---|---|
| ITEM | n | $\bar{X}$ (mg/ml) | S.D. (mg/ml) | C.V. (%) |
| IgG |  | 14.55 | ±0.815 | 5.6 |
| IgM | 10 | 2.44 | ±0.121 | 5.0 |
| IgA |  | 1.33 | ±0.085 | 6.4 |

What is claimed is:

1. An immunoassay for simultaneously quantifying a plurality of different kinds of antigens or antibodies, comprising the steps of:
   (1) providing a plurality of microcapsules having on their outer surfaces an antibody or antigen specific to one kind of antigen or antibody of the plurality of kinds of antigens or antibodies to be quantified, the microcapsules being capable of being lysed by complement activity, each kind of the plurality of kinds of microcapsules containing within the microcapsule a different quantifiable substance which does not interact with another quantifiable substance contained in another kind of microcapsule, and is selective to the antigen or antibody to be quantified;
   (2) mixing the plurality of kinds of the microcapsules, a complement, and a test sample which may contain at least one of the kinds of antigens or antibodies to be tested for; and
   (3) quantifying the quantifiable substances released from the microcapsules simultaneously upon lysis by the complement activity, and wherein said microcapsules are formed of cells capable of containing said quantitatively determinable substance within the capsule defined by the cell membrane.

2. The immunoassay according to claim 1, wherein the microcapsules consist of sheep red blood cell ghosts.

3. The immunoassay according to claim 1, wherein the quantifiable substance is selected from the group of a protein, an enzyme, a polysaccharide or a nucleic acid.

4. The immunoassay according to claim 3, wherein the quantifiable substance is a water-soluble macromolecule and the macromolecule is quantified by means of a molecular sieve.

5. The immunoassay according to claim 1, wherein the plurality of kinds of antigens to be quantified are human immunoglobulins.

6. The immunoassay according to claim 1, wherein the plurality of kinds of antigens to be quantified are cancer markers.

7. The immunoassay according to claim 1, wherein the plurality of kinds of antigens to be quantified are isozymes.

8. The immunoassay according to claim 1, wherein the concentration of each of the quantifiable substances contained in each of the plurality of kinds of microcapsules is substantially proportional to an expected concentration of the corresponding antigen or antibody to be quantified, whereby the quantifiable substances are present in substantially equal amounts at the time of quantification.

* * * * *